United States Patent
Achtmann

(10) Patent No.: US 8,486,432 B2
(45) Date of Patent: Jul. 16, 2013

(54) METHOD OF TREATING ANIMAL'S EXTERIOR FOR CLEANING AND/OR INSECT REPELLENCY

(75) Inventor: Hans Achtmann, Newport, NH (US)

(73) Assignee: Hans P. Achtmann Revocable Trust, New Canaan, CT (US)

( * ) Notice: Subject to any disclaimer, the term of this patent is extended or adjusted under 35 U.S.C. 154(b) by 0 days.

(21) Appl. No.: 13/616,736

(22) Filed: Sep. 14, 2012

(65) Prior Publication Data

US 2013/0012600 A1    Jan. 10, 2013

Related U.S. Application Data

(60) Continuation of application No. 12/912,004, filed on Oct. 26, 2010, which is a continuation of application No. 11/630,138, filed as application No. PCT/US2005/023764 on Jul. 5, 2005, now abandoned, and a continuation-in-part of application No. 10/726,524, filed on Dec. 4, 2003, now Pat. No. 7,223,362, which is a division of application No. 09/987,234, filed on Oct. 29, 2001, now Pat. No. 6,660,698, which is a continuation-in-part of application No. 09/458,678, filed on Dec. 10, 1999, now abandoned, which is a continuation-in-part of application No. 09/081,461, filed on May 19, 1998, now abandoned, which is a continuation-in-part of application No. 08/701,063, filed on Aug. 21, 1996, now Pat. No. 5,753,127.

(60) Provisional application No. 60/585,085, filed on Jul. 6, 2004.

(51) Int. Cl.
*A61K 47/16*  (2006.01)
*A61K 47/12*  (2006.01)
*A61P 33/14*  (2006.01)
*A01N 25/04*  (2006.01)
*A01N 37/06*  (2006.01)
*A01N 25/30*  (2006.01)

(52) U.S. Cl.
USPC .......................................... 424/405; 514/784

(58) Field of Classification Search
USPC .......................................................... 424/405
See application file for complete search history.

(56) References Cited

U.S. PATENT DOCUMENTS 5,474,712 A * 12/1995 Dotolo et al. ................. 510/160

* cited by examiner

*Primary Examiner* — Richard Schnizer
*Assistant Examiner* — Audrea Buckley
(74) *Attorney, Agent, or Firm* — Clark & Brody

(57) ABSTRACT

A method of treating animals to reduce the presence of annoying insects around the animal, help clean the animal's exterior, add luster and sheen to the animal's coat or hide, and provide stain repellency includes the application of a gelled composition to the exterior of an animal. The composition includes a nonionic primary surfactant comprising an ethoxylated sorbitol oleate, a nonionic secondary surfactant, and water. The nonionic secondary surfactant is selected from the group consisting of linear ethoxylated secondary alcohols, polyoxyethylene ethers, ethoxylated sorbitan monolaurates, ethoxylated fatty acid amides and ethoxylated fatty acids that contain about 7 moles to about 26 moles of ethylene oxide and comprise from about 20 to about 36 weight percent of said composition. The water is in a sufficient amount so that the nonionic primary and secondary surfactants together with the water form a gel.

11 Claims, No Drawings

METHOD OF TREATING ANIMAL'S EXTERIOR FOR CLEANING AND/OR INSECT REPELLENCY

This application is a continuation of application Ser. No. 12/912,004 filed on Oct. 26, 2010, which is a continuation of application Ser. No. 11/630,138 filed on Dec. 20, 2006, which is a National Stage application of PCT/US2005/023764 filed Jul. 5, 2005 and claims priority under 35 USC 119(e) based on provisional application No. 60/585,085 filed on Jul. 6, 2004.

FIELD OF THE INVENTION

The present invention is related to an improved method of treating an animal's exterior, and in particular to one that provides one or more of cleansing, insect repellency, stain repellency, and luster enhancement, and is a method that is particularly effective in deterring flies and ticks from a horse's hide.

BACKGROUND ART

It is well known that flies and ticks are attracted to horses and other animals, and are also a nuisance to humans when humans are working on or are around the animals.

Thus, it would be highly beneficial if one were able to keep these insects away from animals, and particularly for only a short period of time, e.g., an hour or two, so that the animals could be properly worked on.

The present invention solves this problem by providing a method for cleansing or shampooing the animal's hide/skin/fur, as well as imparting insect repellency to insects such as flies and ticks.

The inventive method employs a gelled surfactant-containing composition that was previously used for emulsifying oil, particularly oil resulting from a spill. This composition is disclosed in U.S. Pat. Nos. 5,753,127 and 6,660,698 to Riley, each of which is hereby incorporated by reference in its entirety. However, there was never any recognition of the ability of this composition to be effective in reducing the attraction of flies and ticks to animals, and particularly horses.

SUMMARY OF THE INVENTION

One object of the invention is a method of treating an animal exterior for cleaning and/or reducing the attraction of insects, particularly flies and ticks, to the animal.

Another object of the present invention is a method of treating an animal's exterior that is effective for increasing the sheen or luster to an animal's hide or fur or provide stain repellency.

Yet another object of the invention is the use of the composition as a horse cleaner or shampoo.

Other objects and advantages of the present invention will become apparent as a description of the invention proceeds.

In satisfaction of the foregoing objects and advantages, the present invention provides improvements in the treatment of animals for insect repellency, cleaning, improving luster/sheen, and stain repellency. According to the method, a surfactant composition is provided in gel form and applied to the animal's exterior. The surfactant composition comprises a nonionic primary surfactant comprising an ethoxylated sorbitol oleate and a nonionic secondary surfactant selected from the group consisting of linear ethoxylated secondary alcohols, polyoxyethylene ethers, ethoxylated sorbitan monolaurates, ethoxylated fatty acid amides and ethoxylated fatty acids and containing about 7 moles to about 26 moles of ethylene oxide and comprising from about 20 to about 36 weight percent of the composition. The nonionic secondary surfactant is capable of stabilizing and solubilizing the nonionic primary surfactant such that the composition has a hydrophilic/lipophilic balance between about 12.0 and about 13.5. The composition also includes water in a sufficient amount so that the nonionic primary and secondary surfactants together with the water form a gel. The composition is applied to the animal's exterior for the purpose of one or more of cleaning, imparting an insect repellency, imparting luster to the animal's coat, or to provide stain repellency to the animal's exterior.

While the animal could be any type of an animal, preferred animals for treatment are horses.

The composition can be used in an undiluted condition by directly applying it to the animal to be treated, or if so desired, the composition can be further diluted with water prior to the applying step. While virtually any dilution rate can be employed, a preferred ratio of composition to water is 1-5 ounces of composition to be diluted with 1-5 gallons of water. A pad, sponge, brush or other means can be used to assist in applying the composition to the animal's exterior.

A preferred primary surfactant for the composition is ethoxylated sorbitol septaoleate and a preferred hydrophilic/lipophilic balance for the secondary surfactant is from about 10 to about 17. The composition can also contain an emulsion-stabilizing agent and/or a polyethylene glycol component having a molecular weight of from about 200 to about 400. A preferred water content is between about 30-33% by weight of the total composition.

DESCRIPTION OF THE PREFERRED EMBODIMENTS

The present invention offers significant advantages to animals and those persons working on animals in its ability to repel insects, and particularly flies and ticks, from the animal's exterior. The repellent nature of the skin treatment composition can provide the animal with an extended period of time wherein flies or ticks do not light onto the horse. This is advantageous in reducing the occurrences of ticks embedding themselves in the animal, thus requiring treatment, and reducing the fly population hovering around the animal, particularly horses. The applied composition is also believed to act as a liquid band-aid to bruises and cuts in the form of an antibiotic/antiseptic.

The invention uses the composition disclosed in the aforementioned U.S. Pat. Nos. 5,753,127 and 6,660,698 to Riley. More specifically, it has been discovered that the petroleum emulsifying and odor eliminating composition of the Riley patents (hereinafter the composition) is effective in repelling insects such as flies and ticks from animals, particularly horses. It is believed that application of the Riley composition to the animal's exterior prevents gases and oils from emanating from the animal's body. It is these gases and oils that attract the insects, and with their elimination, the insects are not attracted to the animal, and the composition effectively removes the attractants that lure the flies, ticks and other insects to the animal's exterior. For purposes of this application, the removal of the attraction of insects by preventing escape of the oils and gases is considered to be an insect repellent feature.

While the Riley patents are incorporated by reference, a further description is provided herein. In the Riley composition, the primary surfactant ingredient is an ethoxylated sorbitol oleate and more preferably is a composition comprised of a mixture of ethoxylated sorbitol oleates. That is to say that such ethoxylated sorbitol oleate mixtures will have a first ethoxylated sorbitol oleate and at least one other ethoxylated sorbitol oleate. In one particularly preferred mixture, the first ethoxylated sorbitol oleate is ethoxylated sorbitol septaoleate and the second ethoxylated sorbitol oleate is an ethoxylated sorbitol oleate selected from the group consisting of ethoxylated sorbitol trioleate and ethoxylated sorbitol hexaoleate. Most preferably, the nonionic, primary surfactant will comprise from about 45 to about 90 weight percent of the overall end product composition as it is manufactured but before it is diluted with water in the field, if necessary.

The secondary surfactant ingredient of the Riley patent is most preferably a nonionic surfactant, or mixture of nonionic surfactants and especially those nonionic surfactants having a hydrophilic/lipophilic balance (HLB) of about 10 to about 17. Most preferably, the secondary surfactants of the herein-described compositions will be selected from the group consisting of linear ethoxylated secondary alcohols, polyoxyethylene aryl ether, ethoxylated fatty acid amides, ethoxylated fatty acids and ethoxylated sorbitan monolaurate. Such linear ethoxylated secondary alcohols, if employed, preferably will contain from about 7 moles to about 11 moles of ethylene oxide and have an HLB of about 10 to about 15. If so employed, a polyoxyethylene aryl ether ingredient will most preferably have an HLB greater than 15.5. An ethoxylated sorbitan monolaurate ingredient will, preferably, contain from about 15 moles to about 26 moles of ethylene oxide and have an HLB of about 15 to about 17. The Riley compositions preferably will contain from about 20 to about 36 weight percent (as such compositions are produced, but before they are further diluted, if they are in fact further diluted, prior to use in the field) of such a nonionic, secondary surfactant (or mixture of such surfactants). The secondary surfactant also should be capable of stabilizing and solubilizing the primary surfactant to an extent such that the resulting manufactured composition for emulsifying a petroleum product has an HLB from about 12.0 to about 13.5.

The water component disclosed in the Riley patent may be inherently added to the composition as part of the manufacturing process by virtue of the fact that water may be a component of applicant's oleate ingredient(s) (e.g., about 25 to 35% thereof) and/or by virtue of the fact that water is added as a distinct ingredient in the manufacturing process. According to the Riley patents, the water in the oleate ingredients and/or secondary surfactant ingredient(s) and/or the water added as a distinct ingredient in a separate step in the manufacturing process will be in quantities such that the resulting emulsifying compositions, as they are manufactured, will comprise from about 0.05 to about 30 or weight percent water. The water component of the manufactured compositions (i.e., before any addition of water to such manufactured compositions is carried out in the field) will preferably be less than about 30 weight percent of the manufactured product, and even more preferably will constitute less than 20 weight percent of such manufactured products. A separate water component used in the manufacturing process (if any is in fact used) is preferably de-ionized water, but fresh water or even salt water may be employed for this purpose.

Certain optional components also may be part of the Riley composition. These optional components preferably include an emulsion-stabilizing agent and/or a polyethylene glycol composition (and especially a polyethylene glycol having a molecular weight from about 200 to about 400). The composition, as manufactured, but it is diluted, can preferably contain from about 1.0 weight percent to about 4.0 weight percent of the emulsion-stabilizing, agent, and from about 1.0 weight percent to about 2.0 weight percent of the polyethylene glycol ingredient. When any, or all, of these optional ingredients are employed, it is highly preferred that resulting compositions have the 12.0 to 13.5 HLB value sought in those compositions that do not contain any optional ingredients. It also should be noted that, regardless of whether or not these optional ingredients are employed, the end product compositions are also particularly characterized by their ready biodegradability, low levels of toxicity to the environment, wide range of thermal stability, ease of use (owing to the fact that they can be premixed long before use without undergoing intervening phase separation).

To further enhance the rate of biodegradation of the Riley compositions in situations where nitrogen, phosphorus and oxygen, small amounts of inorganic, commercially available fertilizers, such as mixtures of urea formaldehyde and potassium orthophosphates, also may be added as additional optional ingredients. These optional fertilizer ingredients are preferably dissolved in water and added to the Riley composition (again, before such products are diluted in the field) in concentrations such that no one of them forms more than about 0.5% of the total weight of the pre-field diluted emulsifying compositions of this patent disclosure. If it is also desired to lower the freezing point of these emulsifying compositions, a nontoxic solvent such as, for example, diethylene glycol monobutyl ether also may be added as yet another optional ingredient. This ingredient, if used at all, will be added in concentrations such that the diethylene glycol monobutyl ether constitutes from about 1.0 to about 10.0 weight percent of the manufactured, end product composition.

In some of the most preferred compositions, prior to any field dilution, the ethoxylated sorbitol oleate ingredient will be a mixture of ethoxylated sorbitol oleates comprising (1) about 45 to about 50 weight percent of a first ethoxylated sorbitol oleate such as ethoxylated sorbitol septaoleate and wherein said ethoxylated sorbitol oleate contains from about 35 moles to about 45 moles of ethylene oxide; and (2) from about 9 to about 10 weight percent of a second ethoxylated sorbitol oleate, and especially those selected from the group of oleates consisting of ethoxylated sorbitol trioleate and ethoxylated sorbitol hexaoleate. Ethoxylated sorbitol trioleate and ethoxylated sorbitol hexaoleate ingredients containing about 40 moles to about 50 moles of ethylene oxide are particularly effective as second, or co-surfactant, ethoxylated sorbitol oleates. The remainder of these most preferred compositions will be comprised of from about 20 to about 36 weight percent of the secondary surfactant and from about 0.05 to about 30.0 weight percent water.

Good emulsification results are obtained when the secondary surfactant of the present invention stabilizes and solubilizes the primary surfactant composition to a degree such that the manufactured end product compositions (before any field dilution of such manufactured compositions takes place) have a hydrophilic/lipophilic balance (HLB) between about 12.0 and about 13.5. Those skilled in this art will appreciate that the term "HLB" as used herein is a well-known measure of the relative hydrophilicity or lipophilicity of a surfactant composition. Generally speaking, HLB values are obtained by dividing the molecular weight of the hydrophilic component of a compound by the molecular weight of the compound and multiplying the resulting number by selected adjuster values known to those skilled in this art. HLB values range on a scale from 1 to more than 20, with 1 indicating the least hydrophilic and 20 and above indicating the most hydrophilic.

As noted above, the stability of the compositions can be increased when small amounts of the emulsion-stabilizing agent are included in applicant's compositions. These emulsion-stabilizing agents are often used to provide steric stabilization of dispersed particles (for example, literature published by Imperial Chemical Industries PLC (ICI) suggests use of their Hypermer A409® and Hypermer A394® compositions for this purpose). Applicant has, however, found that the inclusion of such emulsion-stabilizing agents in the herein-described compositions greatly increases the stability of the composition. Some of the better descriptions of such emulsion-stabilizing agents are found in the technical literature published by their manufacturers, and therefore, applicant hereby incorporates by reference the following publication describing the properties of ICI's Hypermer® Polymeric Surfactants and Dispersants for Industrial Applications", ICI Americas Inc., 1994.

To prepare the emulsifying compositions of the Riley patents, the primary surfactant composition is preferably made by first combining the first and the second ethoxylated sorbitol oleates under light, non-aerating agitation. If desired, the emulsion-stabilizing agent and/or the polyethylene glycol are combined under moderately high shear conditions and then blended with the primary surfactant composition. In some of the more preferred embodiments of this invention, the secondary surfactant is added to the primary surfactant composition by blending it under non-aerating shear conditions. Finally, the water component is preferably added by blending under low shear conditions. Again, it should be understood that additional water can be incorporated into the manufactured compositions at a later time, e.g., just prior to use, so that smaller volumes of the manufactured compositions may be transported to a spill site.

The composition for use in the invention in one mode comprises:

(a) a nonionic primary surfactant comprising an ethoxylated sorbitol oleate;

(b) a nonionic secondary surfactant selected from the group consisting of linear ethoxylated secondary alcohols, polyoxyethylene ethers, ethoxylated sorbitan monolaurates, ethoxylated fatty acid amides and ethoxylated fatty acids and containing about 7 moles to about 26 moles of ethylene oxide and comprising from about 20 to about 36 weight percent of said composition, and wherein said nonionic secondary surfactant is capable of stabilizing and solubilizing said nonionic primary surfactant such that said composition has a hydrophilic/lipophilic balance between about 12.0 and about 13.5; and (c) water.

The primary surfactant can be ethoxylated sorbitol septaoleate. The secondary surfactant has a hydrophilic/lipophilic balance of from about 10 to about 17. The composition can further comprise an emulsion-stabilizing agent. The composition can further comprise a polyethylene glycol component having a molecular weight of from about 200 to about 400.

A preferred form of the composition for use as an animal skin cleansing agent and insect repellent and that falls within the Riley patents is the product sold as Biodispers, available from Petrotech America Corporation of Newport, N.H., and formulated under the Riley patents. The water content of the composition for use in the invention should be that amount that causes the composition to reach its gel point. When using the Biodispers specific formulation, the water content needed for reaching the gel point is around 30-33%, with a target of around 32%. Of course, the water content could vary depending on the exact formulation of the composition as taught in the Riley patents that is employed in the instant invention, but it should be that amount to allow the composition to reach the gel point, i.e., form a gel. Thus, the water content could fall within the range disclosed in the Riley patents of up to 30% water, but it could also exceed that amount, e.g., be up to 33% in order to attain the desired gelling.

In one mode of the invention, the gelled composition of the invention can be used in effective amounts directly on the animal for treatment. In this mode, the composition can be preferably applied to an animal by direct application and without any other aids such as a pad, cloth, sponge or the like. Alternatively, the composition can be used by first impregnating an absorbent material such as a pad or sponge with the composition and wiping it on the animal. Of course, other known means of application of the gelled composition can be employed, the use of brushes or any other implement that would retain the composition for application to an animal's exterior.

In an alternative mode, the gelled composition is diluted with water and applied to an animal, either directly or with the aid of an implement such as a pad, brush, sponge, or the like. Preferably, the gelled composition is diluted with water at a ratio of 1-5 ounces of gelled composition to 1-5 gallons of water. The animal can then be washed on a routine basis with the diluted composition. When diluting the gelled composition, an effective amount of the gelled composition in the diluted solution is that amount that when applied to the animal's exterior, insects such as flies and ticks are not attracted to the animal's exterior. Again, it is believed that the gelled composition functions such that the odor (gases and liquids) emanating from the animal's exterior is suppressed to the point where the insect does not sense the odor, and is thus not attracted to the animal. A side effect of this phenomenon is that the insects in the area of the animal then become attracted to other odors that are present, and if humans are in the area, they may encounter an increased number of insects in their vicinity.

To test the efficacy of the insect repellency when the gelled composition is used on animals, horses in a stable were treated with the diluted gelled composition in the same manner as they would be with a regular shampoo. At the onset of the test, target times for the repellency of flies from the horses were between 1 and 2 hours. Observing the horses over time, the horse's exterior were, and quite unexpectedly, essentially fly and tick-free for more than 60 hours.

It was also noted during this testing that the horse's hide exhibited a sheen and luster that was comparable to the hide after being treated with typical glossing agents that are commonly used on horses or other animals. This indicated that the insect repelling component also functioned as luster enhancing agent.

On white horses, it was also noted that the hide in the lower leg areas was conspicuously absent of manure stains, thus indicating that the composition when used on horses also has some stain repellency characteristics as well.

Advantages of the composition include that it is odorless, has a neutral pH, and is low foaming or non-sudsy. The composition will generally not strip the natural oil from an animal's skin or coat. As noted above, it adds luster to the skin or coat, is made of all natural/organic ingredients, and is biodegradable. Because of its safe nature, it is not detrimental to the environment, particularly if it enters run-off waters in the area of treatment of one or more animals. Also, there is no negative impact on the skin due to a lack of alkaloids in the composition, i.e., the composition does not instigate itching or rubbing.

In an exemplary use for treating the hide or a horse, the horse should be first wetted. Then, the composition can be applied directly using a sponge, pad, or brush or first diluted with water as explained above, and then applied with a sponge, brush, pad or the like. The composition is scrubbed over the animal's hide, rinsed off and the animal coat is allowed to dry. One means of application would be a mitt or glove (similar to an oven mitt) that would include an absorbent strip of material held on to the mitt with hook and loop fasteners or otherwise attached to the palm side of the mitt. The composition can be applied to the absorbent material, and then scrubbed onto the animal being treated. Of course, any known applicator can be used to apply the composition, either in its diluted or non-diluted form.

While the application is exemplified for horses, the composition with its cleaning and suppression of gases and odors to achieve insect repellency can be used on virtually any animal where cleaning and/or insect repellency are needed, e.g., dogs, cats, other pets, zoo animals, or the like.

As such an invention has been disclosed in terms of preferred embodiments thereof, which fulfills each and every one of the objects of the invention as set forth above, and provides an improved method of treating animals for cleanliness, luster/sheen, and insect problems.

Of course, various changes, modifications and alterations from the teachings of the present invention may be contemplated by those skilled in the art without departing from the intended spirit and scope thereof. It is intended that the present invention only be limited by the terms of the appended claims.

I claim:

1. A method of treating an exterior of an animal for cleaning and/or to impart insect repellency to the exterior comprising:
   a) providing an insect repelling composition comprising:
      (i) a nonionic primary surfactant comprising an ethoxylated sorbitol oleate;
      (ii) a nonionic secondary surfactant selected from the group consisting of linear ethoxylated secondary alcohols, polyoxyethylene ethers, ethoxylated sorbitan monolaurates, ethoxylated fatty acid amides and ethoxylated fatty acids and containing about 7 moles to about 26 moles of ethylene oxide and comprising from about 20 to about 36 weight percent of said composition, and wherein said nonionic secondary surfactant is capable of stabilizing and solubilizing said nonionic primary surfactant such that said composition has a hydrophilic/lipophilic balance between about 12.0 and about 13.5; and
      (iii) water, wherein the water is in a sufficient amount so that the nonionic primary and secondary surfactants together with the water form a gel; and
   b) applying said insect repelling composition to the animal's exterior for the purpose of cleaning and/or imparting at least insect repellency to the exterior.

2. The method of claim 1, wherein the animal is a horse.

3. The method of claim 1, wherein the composition is diluted with water prior to the applying step.

4. The method of claim 3, wherein the composition is diluted using a ratio of 1-5 ounces of the composition to 1-5 gallons of water prior to using the composition in the applying step.

5. The method of claim 1, wherein the composition is applied to one of an absorbent pad, sponge, or brush that is then applied to the animal.

6. The method of claim 2, wherein the composition is applied to one of an absorbent pad, sponge, or brush that is then applied to the animal.

7. The method of claim 1, wherein the primary surfactant is ethoxylated sorbitol septaoleate.

8. The method of claim 1, wherein the secondary surfactant has a hydrophilic/lipophilic balance of from about 10 to about 17.

9. The method of claim 1, wherein the composition further comprises an emulsion-stabilizing agent.

10. The method of claim 1, wherein the composition further comprises a polyethylene glycol component having a molecular weight of from about 200 to about 400.

11. The method of claim 1, wherein the water content comprises 30-33% by weight of the total composition.

* * * * *

UNITED STATES PATENT AND TRADEMARK OFFICE
CERTIFICATE OF CORRECTION

PATENT NO. : 8,486,432 B2
APPLICATION NO. : 13/616736
DATED : July 16, 2013
INVENTOR(S) : Hans P. Achtmann Page 1 of 1

It is certified that error appears in the above-identified patent and that said Letters Patent is hereby corrected as shown below:

Title page, Related U.S. Application Data item [60] should read as follows:

This application is a continuation of application serial no. 12/912,004 filed on October 26, 2010, which is a continuation of application no. 11/630,138 filed on December 20, 2006, which is a National Stage application of PCT/US2005/023764 filed July 5, 2005 and claims priority under 35 USC 119(e) based on provisional application no. 60/585,085 filed on July 6, 2004.

Signed and Sealed this
Thirtieth Day of December, 2014

Michelle K. Lee
*Deputy Director of the United States Patent and Trademark Office*